(12) United States Patent
Ferris

(10) Patent No.: US 6,397,837 B1
(45) Date of Patent: Jun. 4, 2002

(54) INHALER ASSISTIVE DEVICE

(76) Inventor: Martin W. Ferris, 6218 Acorn Dr., Emmaus, PA (US) 18049

( * ) Notice: Subject to any disclaimer, the term of this patent is extended or adjusted under 35 U.S.C. 154(b) by 0 days.

(21) Appl. No.: 09/359,558

(22) Filed: Jul. 22, 1999

(51) Int. Cl.[7] ............................................. A61M 11/00
(52) U.S. Cl. ............................. 128/200.14; 128/200.23
(58) Field of Search ........................ 128/200.14, 200.22, 128/200.23

(56) References Cited

U.S. PATENT DOCUMENTS

| | | | | |
|---|---|---|---|---|
| 3,119,557 A | * | 1/1964 | Chapman ................ | 128/200.23 |
| 3,456,644 A | | 7/1969 | Thiel | |
| 3,456,645 A | | 7/1969 | Brock | |
| 3,565,070 A | | 2/1971 | Hanson et al. | |
| 3,610,480 A | * | 10/1971 | Lipfert ................... | 128/200.23 |
| 3,625,403 A | * | 12/1971 | Rousselot .............. | 128/200.23 |
| 3,636,949 A | | 1/1972 | Kropp | |
| 3,789,843 A | | 2/1974 | Armstrong et al. | |
| 3,826,413 A | * | 7/1974 | Warren ................... | 128/200.23 |
| 3,994,421 A | * | 11/1976 | Hansen ................... | 128/200.23 |
| 4,576,157 A | | 3/1986 | Raghuprasad | |
| 4,648,393 A | | 3/1987 | Landis et al. | |
| 4,678,106 A | * | 7/1987 | Newell et al. ......... | 128/200.23 |
| 4,796,614 A | * | 1/1989 | Nawacki et al. ....... | 128/200.23 |
| 4,834,083 A | * | 5/1989 | Byram et al. .......... | 128/200.23 |
| 4,860,738 A | * | 8/1989 | Hegemann et al. .... | 128/200.22 |
| 4,953,545 A | * | 9/1990 | McCarty ................ | 128/200.23 |
| 5,133,343 A | | 7/1992 | Johnson, IV et al. | |
| 5,184,761 A | * | 2/1993 | Lee ........................ | 128/200.23 |
| 5,203,323 A | * | 4/1993 | Tritle ..................... | 128/200.23 |
| 5,392,768 A | * | 2/1995 | Johansson et al. ..... | 128/200.23 |
| 5,427,089 A | * | 6/1995 | Kraemer ................ | 128/200.23 |

* cited by examiner

Primary Examiner—Aaron J. Lewis
(74) Attorney, Agent, or Firm—Ratner & Prestia

(57) ABSTRACT

Method and apparatus for enabling a user having reduced manual dexterity and/or strength to operate an aerosol inhaler by modifying the inhaler to have a lever juxtaposed adjacent the flat end of the aerosol cannister, or inserting an inhaler into a device having a lever juxtaposed to the flat end of the aerosol cannister, the lever adapted to be moved by the user to depress the aerosol cannister and dispense medication contained in said aerosol cannister.

2 Claims, 5 Drawing Sheets

US 6,397,837 B1

INHALER ASSISTIVE DEVICE

CROSS REFERENCE TO RELATED APPLICATIONS

Not Applicable

STATEMENT REGARDING FEDERALLY SPONSORED RESEARCH OR DEVELOPMENT

Not applicable

BACKGROUND OF THE INVENTION

The present invention pertains to portable inhalation devices for permitting a user to inhale a medicated vapor spray, which may include powders, liquids, or gases, and in particular to means for assisting actuation of such devices.

People suffering from asthma and other respiratory diseases or disabilities have difficulty breathing from time to time, the breathing difficulty depending upon the activity in which the person with the respiratory disease is engaged in, the degree of inflammation of respiratory tissues and other stresses the individual may be under. A number of medications are available to alleviate the debilitating symptoms or to restore normal breathing. A large number of these medications are dispensed from aerosol-like dispensers as a vapor to be inhaled directly into the lungs of the person needing medication. The dispenser may include an outlet port which the user places in the mouth, the lips providing a seal to ensure passage of the medication through the users mouth for inhalation into his or her lungs. Actuation of the devices generally requires a compressive force exerted on the aerosol container by the users hand, after the outlet port is placed within the mouth.

Conventional dispensers are usually two piece structures, consisting of a housing which contains the mouthpiece which is also adapted to receive the aerosol cannister (can) which contains the medication under pressure. The aerosol can is inserted into the housing so that the outlet of the aerosol can is pointed down or oriented downward with the outlet adjacent the mouthpiece of the housing with the opposite or bottom end of the aerosol can projecting upwardly. The user then can place the housing between the thumb and forefinger and use the thumb and forefinger or the thumb and fingers to force the can downwardly thus releasing a burst of the medicated spray into the mouthpiece of the housing.

For persons having normal manual dexterity and strength actuation of the spray is not a problem. However, there are a number of people who must use inhalers that may also suffer from debilitating effects and limitations which result from such joint diseases such as arthritis. Many of these people no longer have the requisite strength or manual dexterity to compress the inhalers. In order to aid those persons with less than requisite manual dexterity a number of devices have been proposed.

U.S. Pat. Nos. 3,456,644, 3,456,645, 3,636,949, 3,565,070, 3,789,843, 3,826,413, 4,576,157 and 4,648,393 are representative of the state of the art of inhalation devices featuring various types of actuation mechanism.

U.S. Pat. No. 5,133,343 is drawn to a inhalation device that is directed to the problem of an inhaler that can be actuated by a person with less than the requisite manual dexterity or strength.

SUMMARY OF THE INVENTION

The present invention pertains to inhaler assistive devices that can be accomplished by either a separate apparatus that can be used with conventional inhalers without modification of the convention inhaler, or modification of the housing of the conventional inhaler that receives the aerosol container. In either case a simple lever mechanism is used to provide increased mechanical advantage to the user of the inhaler so that a user with less than requisite manual dexterity and/or strength can actuate the inhaler with ease and comfort.

Therefore, in one aspect, the present invention is an apparatus for enabling a user having diminished manual dexterity to use an inhaler of the type having a housing to removeably receive an aerosol can, the can having a medication discharge end opposite a generally flat end, the can containing medication under pressure, the housing having a mouthpiece to direct medication into the mouth of the user when the user applies pressure to the flat end of the can inserted in the housing, the improvement comprising: a generally elongated body adapted to receiving and hold the housing and the can so that the user can position the mouthpiece for dispensing of the medication, the body having a portion projecting above the bottom of the aerosol can; means in the portion of the body projecting above the bottom of the aerosol can to enable a user to effect greater pressure on the flat end of the can than the user, with diminished strength or manual dexterity, could produce manually.

In another aspect, the present invention is an apparatus for enabling a user having diminished strength or manual dexterity to use an inhaler of the type having a housing to removeably receive an aerosol can, the can having a medication discharge end opposite a generally flat end, the can containing medication under pressure, the housing having a mouthpiece to direct medication into the mouth of the user when the user applies pressure to the bottom of the can inserted in the housing, the improvement comprising: a body adapted to surround and frictionally engage a portion of the housing, the body adapted to support means to enable a user to effect greater pressure on the flat end of the can than the user, with diminished manual dexterity, could produce manually.

In still another aspect, the present invention is an apparatus for enabling a user having diminished strength or manual dexterity to use an inhaler of the type having a housing to removeably receive an aerosol can, the can having a medication discharge end opposite a generally flat end, the can containing medication under pressure, the housing having a mouthpiece to direct medication into the mouth of the user when the user applies pressure to the bottom of the can inserted in the housing, the improvement comprising: constructing the housing with a face side extending from the mouthpiece to a location above the bottom of the aerosol can, means in a portion of the face side extending above the bottom of the can to receive means to contact the flat end of the aerosol can the means adapted to permit the user to exert increased force on the flat end of the can to permit dispensing of medication from the can.

In a further aspect, the present invention is an apparatus for enabling a user having diminished strength or manual dexterity to use an inhaler of the type having a housing to removeably receive an aerosol can, the can having a medication discharge end opposite a generally flat end, the can containing medication under pressure, the housing having a mouthpiece to direct medication into the mouth of the user when the user applies pressure to the bottom of the can inserted in the housing, the improvement comprising: force enhancing means adapted to be removeably attached to the housing at a location above the mouthpiece and proximate a face of the housing extending vertically from the mouthpiece the force enhancing means having a generally flat elongated user contact surface portion disposed generally perpendicular to a generally flat extension portion the extension portion having a length so that when the force enhancing means is fixed to the housing the contact surface overlies and projects beyond the flat end of the aerosol can in a direction away from the mouthpiece, whereby when a user exerts force on the contact surface, the force enhancing means causes the aerosol can to dispense the medication.

In an additional aspect, the present invention is an apparatus wherein the force enhancing means includes a pair of mounting arms extending for a portion of the length of and generally parallel to the user contact surface portion with an inwardly projecting pivot fixed to each end of each of the arms opposite to where the extension portion is fixed to the user contact surface portion; and the housing has means to receive the pivots.

In yet another aspect, the present invention is an apparatus for enabling a user having diminished manual dexterity to use an inhaler of the type having a housing to removeably receive an aerosol can, the can having a medication discharge end opposite a generally flat end, the can containing medication under pressure, the housing having a mouthpiece to direct medication into the mouth of the user when the user applies pressure to the bottom of the can inserted in the housing, the improvement comprising: a generally elongated mounting piece adapted to be removeably fixed to the housing, the mounting piece having an aperture at one end, the aperture adapted to removeably and pivotably receive a lever arm, the mounting piece positioned on the housing so that the aperture is above the flat end of the aerosol can; lever means positioned in the mounting piece in contact with the flat end of the aerosol can to enable a user to effect greater pressure on the bottom of the can than the user, with diminished manual dexterity, could produce manually.

BRIEF DESCRIPTION OF THE DRAWINGS

FIG. 3b is a perspective view of an actuation device to be used with the modified inhaler of FIG. 3a.

FIG. 5b is a perspective view of an actuation device according to the present invention adapted to be fitted to the conventional inhaler of FIG. 5a.

FIG. 5c is a perspective view of the device of FIG. 5b assembled on a conventional inhaler according to FIG. 5a.

DETAILED DESCRIPTION OF THE INVENTION

Figure 1C:
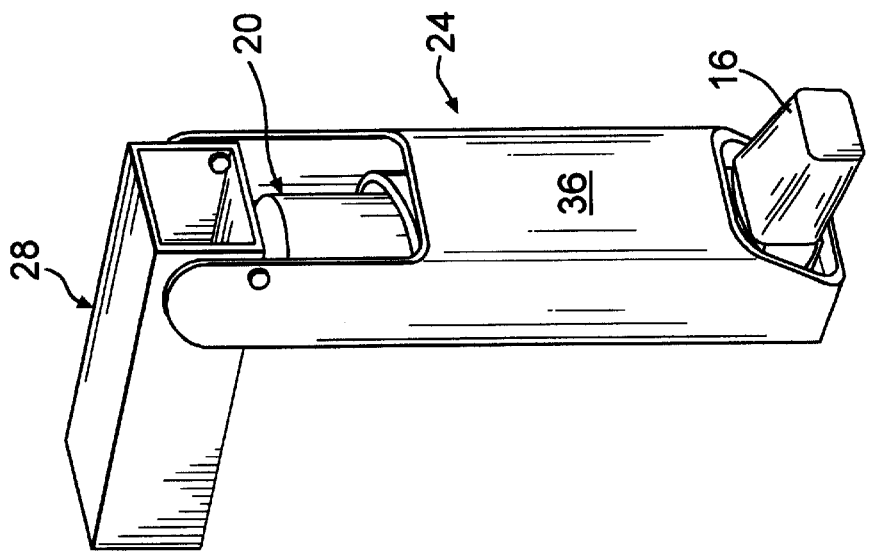
FIG. 1c is a perspective view of the device of FIG. 1b and the conventional inhaler according to the present invention.

Referring to the drawings, wherein like parts have like numbers, the present invention will be described in more detail.

Figure 1B:
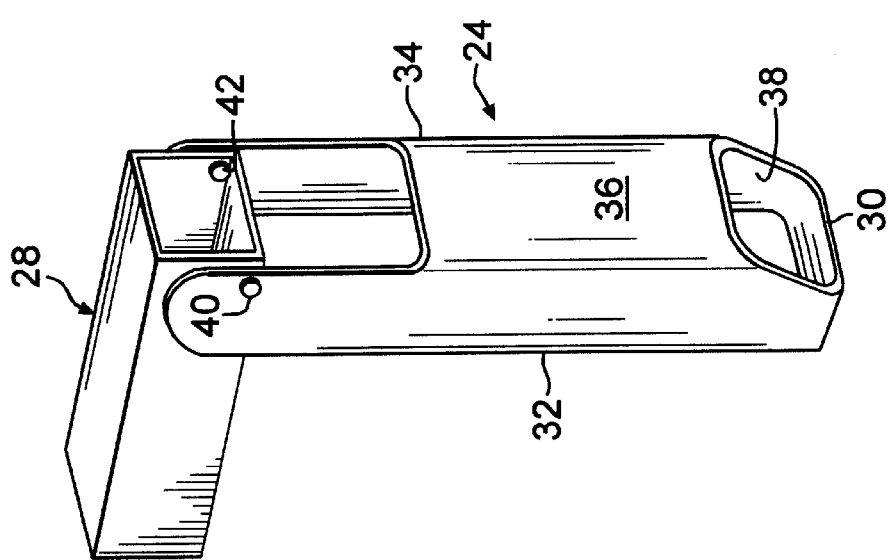
FIG. 1b is a perspective view of a device according to one embodiment of the present invention.
Figure 1A:
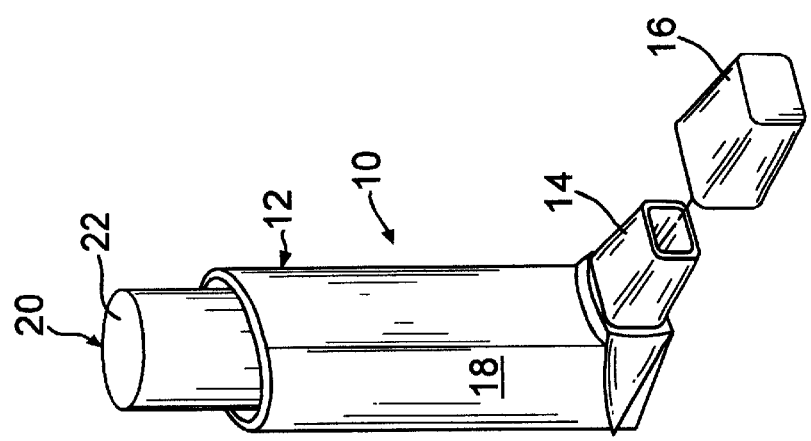
FIG. 1a is a perspective view of a conventional inhaler.

FIG. 1a shows a conventional inhaler 10 consisting of housing 12, with a mouthpiece 14, the mouthpiece 14 adapted to be closed by a mating cover 16. Housing 12 has a body portion 18 which receives an aerosol container 20, the aerosol container 20 having a first end (not shown) and a second or generally flat (bottom) end 22. The first end of the aerosol cannister, can, or receptacle 20 is well known and one type is shown for example in U.S. Pat. No. 3,456,644 the description of which is incorporated herein by reference. Such aerosol cannisters are well known in the art.

FIG. 1b shows a first embodiment 24 of the present invention which includes a body portion 26 and a actuation or lever portion 28. Body portion 26 includes a bottom 30 a pair of vertical sides 32, 34 which project upwardly from the bottom 30 and a front face 36. Face 36 includes a lower opening 38 which is adapted to receive the mouthpiece 14 of inhaler 10 as shown in FIG. 1c. The sides 32, 34 of body 26 contain opposite apertures or pivot points 40 and 42. Pivot points 40, 42 are adapted to receive pins placed in a lower portion of lever 28 so that the lever 28 can pivot vertically around the pivot points 40, 42. The pivoting assembly can be made in any convenient configuration for example the housing can have molded projection which meet with complimenting apertures in the actuation lever.

FIG. 1c depicts the conventional inhaler 10 which is placed inside of the inhaler assistive device 24 of FIG. 1B. The inhaler 10 is placed in the device so the mouthpiece 14 and cover 16 project through the opening 38 in front face 36. The bottom 22 of aerosol cannister 20 fits underneath the lever 28. The lever 28 can be made in any convenient length and when the aerosol dispenser 10 is withdrawn from the body 24 the lever can pivot downwardly to be stored inside of the body 26, thus determining one length for the lever 28. In use, all the person wishing to receive medication has to do is remove the cover 16 place the mouthpiece in their mouth and then press the lever 28 to actuate the dispensing of medicated spray into the users mouth and down into the users lungs. The lever provides a significant mechanical advantage so that those persons with debilitating diseases, such as arthritis, can readily dispense medication without assistance.

Figure 2C:
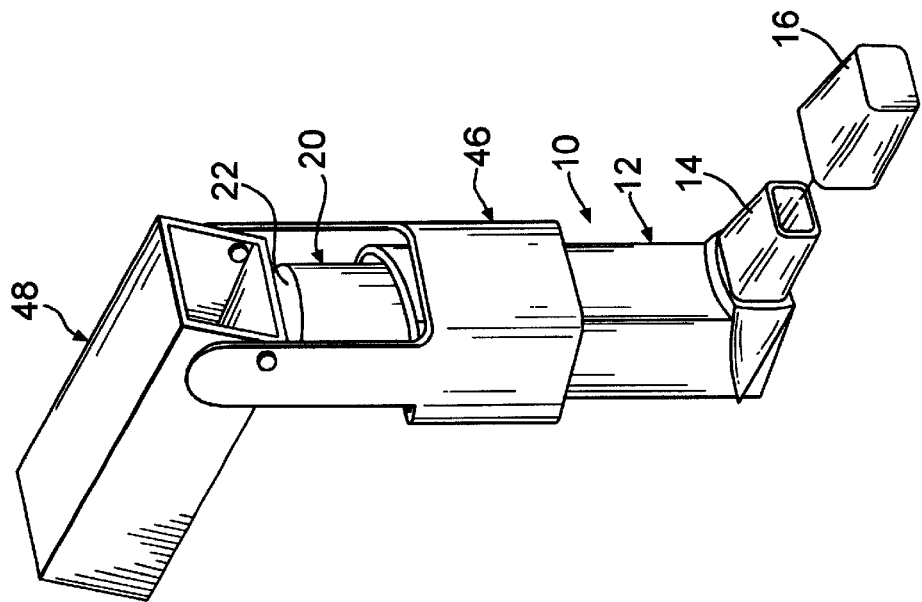
FIG. 2c is a perspective view of the device of FIG. 2b and the conventional inhaler.
Figure 2B:
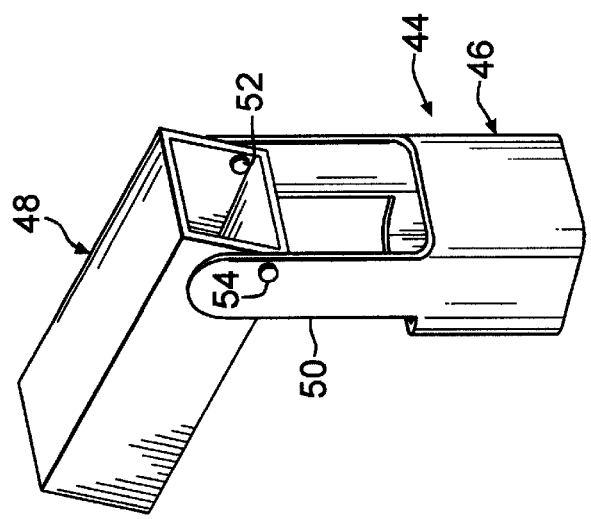
FIG. 2b is a perspective view of a device according to a second embodiment of the present invention.
Figure 2A:
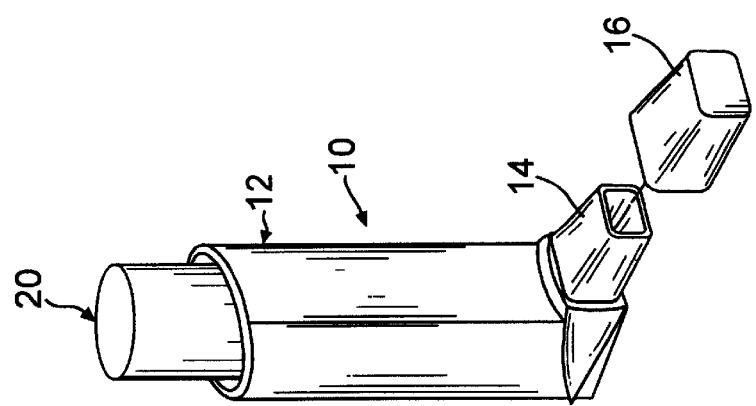
FIG. 2a is a perspective view of a conventional inhaler.

FIG. 2a shows a conventional inhaler 10. FIG. 2b shows an alternate embodiment 44 of the present invention which includes a body portion 46 and a lever 48. Body portion 46 is in the shape of a cylinder which is adapted to slip over the housing 12 of dispenser 10. The body portion 46 fixed be held to the body portion 46 of device 44 either frictionally or with removable cement at the position shown in FIG. 2c.

In FIG. 2b the body portion 46 has two upwardly projecting sides 50, 52 which have pivot points 54, 56 which are adapted to pivotally receive the lever arm 48. As shown in FIG. 2c when the body or collar portion 46 of the assistive device 44 is slipped over the body or housing 12 of dispenser 10 the lever bears against the flat end 22 of aerosol cannister 20. Here again when the user moves the lever 48 in a downward direction the aerosol can is depressed and the medication is dispensed through the mouthpiece 14 of the dispenser 10. The device of FIGS. 2b and 2c provides a significant mechanical advantage, thus enabling a user with less than adequate manual dexterity to dispense medication without assistance.

Figure 3C:
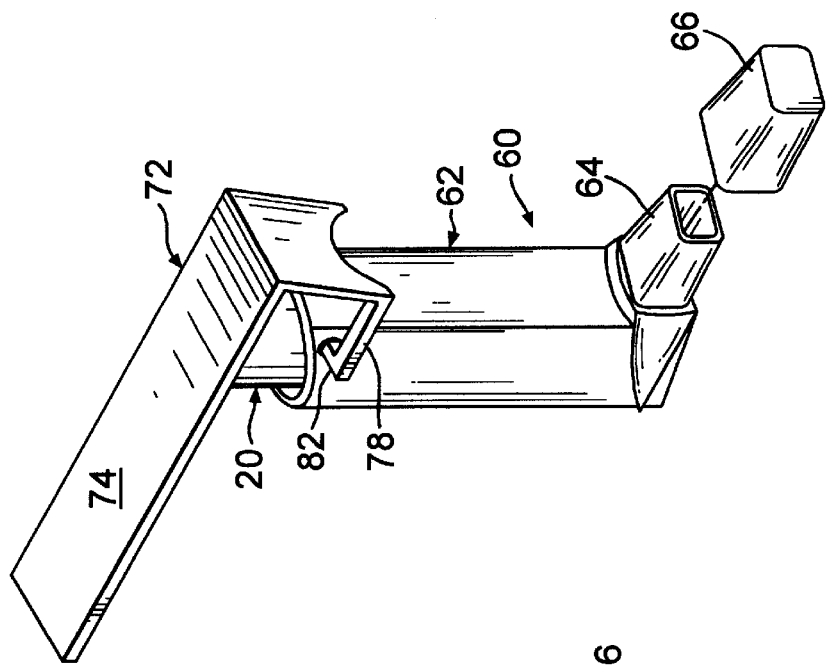
FIG. 3c is a perspective view showing the assembled modified inhaler according to the present invention.
Figure 3B:
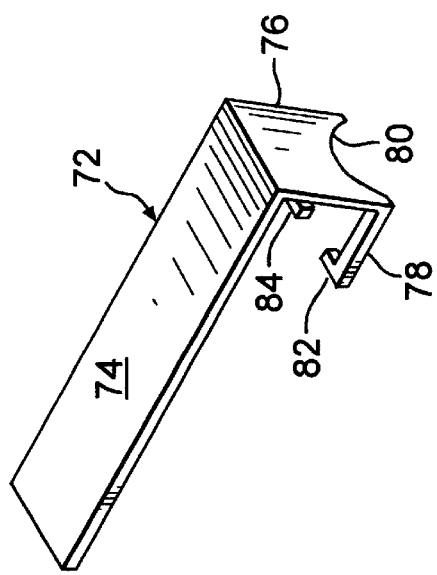
Figure 3A:
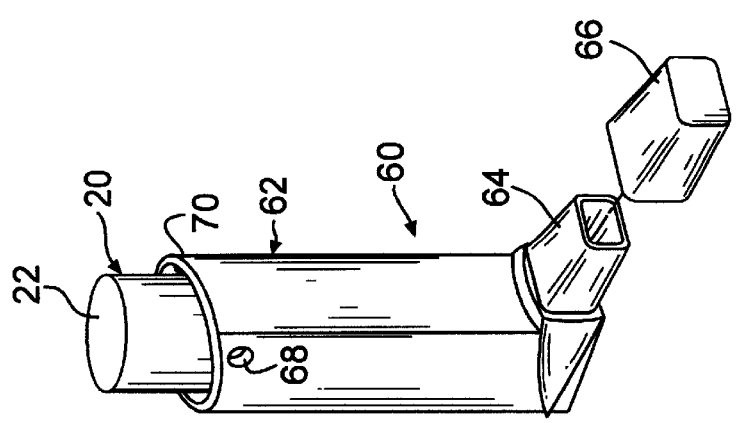
FIG. 3a is a perspective view of a conventional inhaler modified according to the present invention.

FIG. 3a shows a dispenser 60 having a body or housing 62, a mouthpiece 64 with a cover 66, and an aerosol medication cannister 20 having a generally flat end or bottom 22. The body or housing 62 of the dispenser 60 is modified by providing pivot points 68 and 70 on opposite sides of the body 62 so that a lever 72 such as shown in FIG. 3B can be fixed to the body 62. Lever 72 includes a first flat or user contact portion 74 and a vertical face portion 76 which is disposed at right angles to the user contact portion 74 of lever 72. Face portion 76 is of sufficient length so that the contact portion 74 can contact the bottom 22 of aerosol cannister 20 and the lever 72 can be fixed to the body 62 of the dispenser 60 by a pair of parallel mounting arms 78 and 80 which terminate in inwardly projecting pins 82, 84, the pins 82, 84 adapted to fit into the apertures 68 and 70 on body 62 of dispenser 60. As shown in FIG. 3c when the lever is mounted onto the housing 62 of dispenser 60 the user can place his or her hand or a portion thereof or a portion of the lower arm on the contact surface 74 to move the lever in a downward direction to urge the aerosol container downwardly to dispense the medication into the users mouth and lungs. It would also be possible to have projections on the housing instead of apertures 68 and 70 which mate with complimentary shaped depresions or openings in place of pins 82, 84.

Figure 4C:
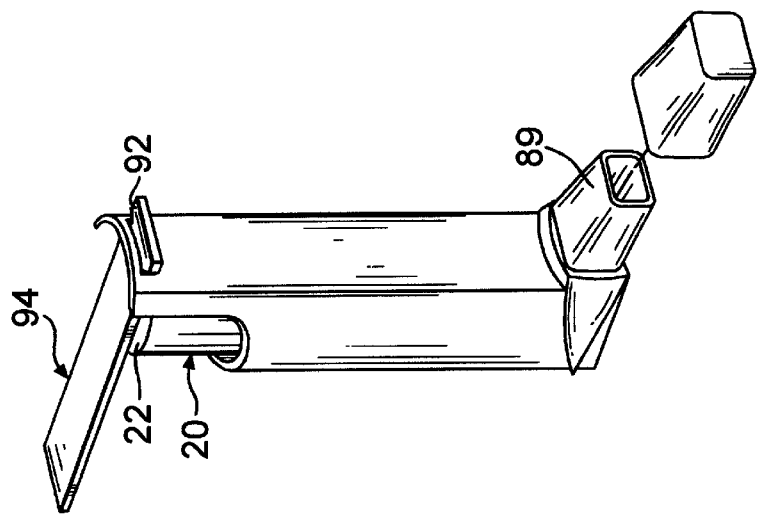
FIG. 4c is a perspective view of the assembled modified inhaler of FIG. 4b.
Figure 4B:
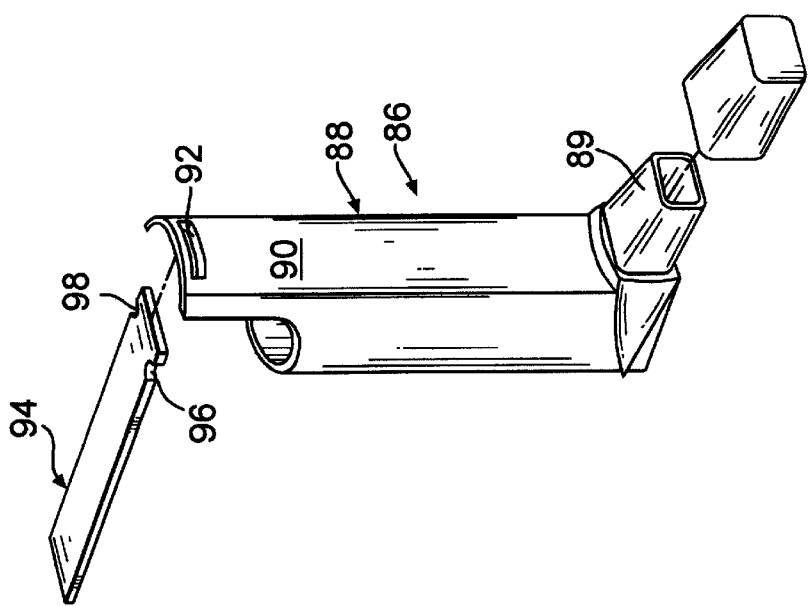
FIG. 4b is a perspective view of the conventional inhaler of FIG. 4a modified according to another aspect of the present invention showing the actuation device separated therefrom.
Figure 4A:
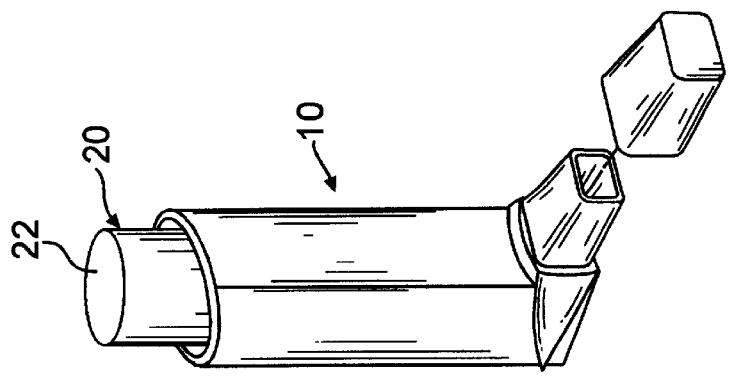
FIG. 4a is a perspective view of a conventional inhaler.

FIG. 4a shows a conventional dispenser 10. FIG. 4b shows a modified housing 88 for dispenser 86. Housing 88 is modified by extending the front face portion 90 vertically to project above the aerosol cannister 20 as shown in FIG. 4c. The portion of the face 90 projecting above the aerosol can has an aperture 92 which is adapted to removably receive a lever arm 94 the front portion of lever arm 94 having suitable cut outs 96, 98 so that the lever arm 94 can be inserted into the aperture 92 as shown in FIG. 4c. The lever arm 94 can be removable for storage or traveling. In use, the device of FIGS. 4b and 4c permits the user to take advantage of the mechanical advantage of the lever to force the aerosol cannister downwardly to dispense medication through the mouthpiece 89 of the housing 88.

Figure 5C:
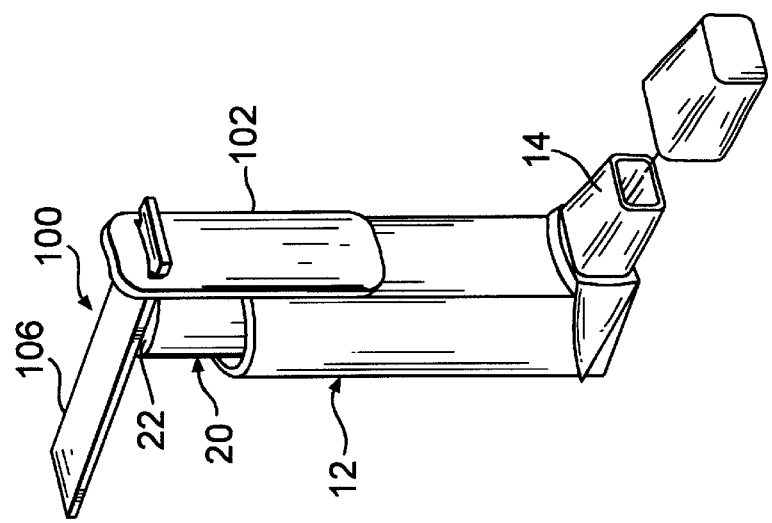
Figure 5B:
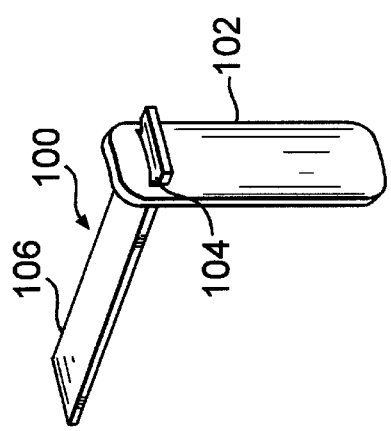
Figure 5A:
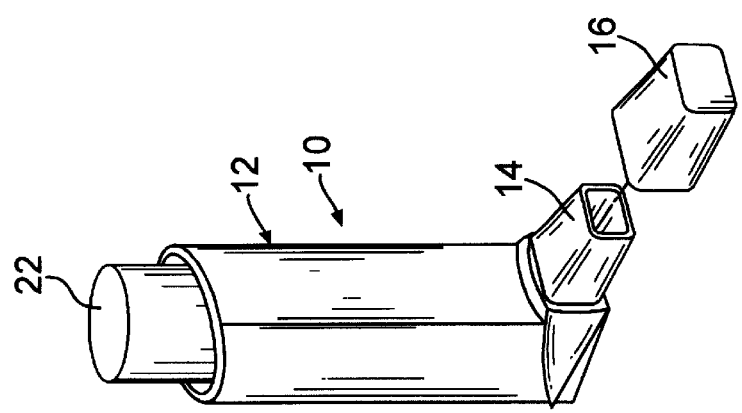
FIG. 5a is a perspective view of a conventional inhaler.

FIG. 5a shows a conventional dispenser 10 with an aerosol container 22 placed in the housing 12. FIG. 5b shows a two piece lever mechanism including a front piece 102 which is adapted to be fixed to the housing 12 by adhesive or other suitable means in the position shown in FIG. 5c. The front piece 102 has slot or aperture 104 similar to the aperture 92 of the FIG. 4b. The lever arm 106 is similar to the lever arm 94 FIG. 4b and is placed in the aperture 104 in a like matter. When the device of FIG. 5b is fixed to the housing 12 the lever can be used by the user to force the aerosol cannister or bottle in a downward direction to dispense medication through the mouthpiece 14 and into the users mouth and lungs.

Materials of construction for devices according to the present invention can be various. One suitable material is polycarbonate resin or other plastics used to fabricate the housing for the aerosol container. Other materials can be metal or even wood so long as the operating characteristics of the invention are achieved.

While the invention has been described and illustrated with respect to an aerosol inhaler where the aerosol cannister is removable or seperable from the housing, the present invention can be used with an aerosol inhaler where the cannister is movable within but not seperable from the housing or where the cannister and housing are a single structure but operate in the same manner as convential inhaler devices, i.e. where a pump like action causes the medicated spray to be dispensed.

Having thus described my invention what is desired to be secured by Letters Patent of the United States is set forth in the appended claims which should be read without limitation.

What is claimed:

1. An accessory apparatus for use with an oral inhalation device for dispensing medication into the lungs of a user, said oral inhalation device consisting of a housing with a mouthpiece arranged laterally respective to said housing, said housing adapted to position an aerosol container containing said medication with a dispensing end of said canister proximate said mouthpiece and a bottom end of said canister opposite said dispensing end projecting above an open end of said housing opposite to said mouthpiece of said housing so that said user having normal dexterity can position said housing with said canister between a thumb and opposed finger to actuate dispensing of said medication by exerting pressure on said bottom end of said canister, said accessory apparatus comprising in combination:

a generally elongated body having a generally flat base portion with two generally parallel sides extending upwardly from said base portion, a face side extending between parallel edges of said sides, said face side having an opening through which said mouthpiece of said housing can be inserted, said sides and said face so constructed and arranged to frictionally hold said housing, said sides extending above said bottom of said aerosol canister when said housing containing said aerosol canister is inserted into said body, said sides adapted to pivotally receive a force enhancing device, said force enhancing device being a generally elongated lever pivotally mounted between said sides of said body projecting above said bottom end of said aerosol canister, said lever extending generally perpendicular to said bottom of said aerosol canister and adapted to exert force on said bottom end of said aerosol canister when said aerosol canister is within said housing within said body, when said lever is moved by said user exerting force on a portion of said lever projecting away from said body;

whereby said user, with diminished manual dexterity and/or diminished strength, can effect greater pressure on said bottom end of said canister than said user, with diminished manual dexterity and/or diminished strength, could produce manually without said apparatus.

2. An accessory apparatus for use with an oral inhalation device for dispensing medication into the lungs of a user, said oral inhalation device consisting of a housing with a mouthpiece arranged laterally respective to said housing, said housing adapted to position an aerosol container containing said medication with a dispensing end of said canister proximate said mouthpiece and a bottom end of said canister opposite said dispensing end projecting above an open end of said housing opposite to said mouthpiece of said housing so that said user having normal dexterity can position said housing with said canister between a thumb and opposed finger to actuate dispensing of said medication by exerting pressure on said bottom end of said canister, said accessory apparatus comprising in combination:

a body having a first portion with the general shape of a collar adapted to slip over and frictionally engage said housing, said collar having a pair of vertically opposed extending surfaces projecting above said bottom of said aerosol canister when said collar portion is positioned on said housing, and a force enhancing means pivotally disposed between said vertically extending surfaces, said force enhancing device being a generally elongated lever pivotally mounted between said sides of said body projecting above said bottom end of said aerosol canister, said lever extending generally perpendicular to said bottom end of said aerosol canister and adapted to exert force on said bottom end of said aerosol canister when said lever is moved by said user exerting force on a portion of said lever projecting away from said body, whereby a user with diminished manual dexterity and/or diminished strength can exert greater pressure on said bottom end of said canister than said user with diminished manual dexterity and/or diminished strength could produce manually without said apparatus.

\* \* \* \* \*

UNITED STATES PATENT AND TRADEMARK OFFICE
CERTIFICATE OF CORRECTION

PATENT NO. : 6,397,837 B1
DATED : June 4, 2002
INVENTOR(S) : Martin W. Ferris

It is certified that error appears in the above-identified patent and that said Letters Patent is hereby corrected as shown below:

Column 1,
Line 36, delete "cannister" and substitute therefor -- canister --

Column 2,
Lines 11, 29, 59 and 65, delete "removeably" and substitute therefor -- removably --

Column 3,
Lines 20, 27 and 29, "removeably" and substitute therefor -- removably --
Line 29, delete "pivotably" and substitute therefor -- pivotally --

Column 4,
Line 18, "cannisters" and substitute therefor -- canisters --
Lines 37 and 62, delete "cannister" and substitute therefor -- canister --

Column 5,
Lines 6, 15, 41, 53, 63 and 66, delete "cannister" and substitute therefor -- canister --

Column 6,
Line 1, delete "cannister" and substitute therefor -- canister --

Signed and Sealed this

Twenty-eighth Day of January, 2003

JAMES E. ROGAN
*Director of the United States Patent and Trademark Office*